United States Patent
Joshi et al.

(10) Patent No.: US 9,168,330 B2
(45) Date of Patent: *Oct. 27, 2015

(54) DEVICE AND METHOD FOR WOUND THERAPY

(71) Applicant: KALYPTO MEDICAL, INC., Mendota Heights, MN (US)

(72) Inventors: Ashok V. Joshi, Salt Lake City, UT (US); John Howard Gordon, Salt Lake City, UT (US); Sai Bhavaraju, West Jordan, UT (US); Troy C. Dayton, Syracuse, UT (US); Jeremy Heiser, Salt Lake City, UT (US)

(73) Assignee: Kalypto Medical, Inc., Mendota Heights, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/912,716

(22) Filed: Jun. 7, 2013

(65) Prior Publication Data

US 2014/0018753 A1    Jan. 16, 2014

Related U.S. Application Data

(60) Continuation of application No. 12/592,049, filed on Nov. 18, 2009, now Pat. No. 8,460,255, which is a division of application No. 11/610,458, filed on Dec. 13, 2006, now Pat. No. 7,779,625, which is a continuation-in-part of application No. 11/432,855, filed on May 11, 2006, now Pat. No. 7,615,036.

(51) Int. Cl.
*A61F 13/20* (2006.01)
*A61M 1/00* (2006.01)
(Continued)

(52) U.S. Cl.
CPC .............. *A61M 1/0088* (2013.01); *A61M 1/009* (2014.02); *A61M 1/0025* (2014.02); *A61M 1/0049* (2013.01); *A61M 1/0031* (2013.01); *A61M 27/00* (2013.01); *A61M 2205/15* (2013.01)

(58) Field of Classification Search
CPC ......... A61F 13/20; A61F 13/00; A61F 13/15; B65D 69/00; B65D 71/00
USPC ......... 604/304–307, 313, 315–317, 541, 543; 602/42, 43, 46

See application file for complete search history.

(56) References Cited

U.S. PATENT DOCUMENTS

| 3,972,328 A | 8/1976 | Chen |
| 4,224,945 A | 9/1980 | Cohen |

(Continued)

FOREIGN PATENT DOCUMENTS

| DE | 20 2004 017 052 | 7/2005 |
| DE | 20 2004 017 052 U1 | 7/2005 |

(Continued)

OTHER PUBLICATIONS

Communication of Notice of Opposition dated Jul. 23, 2014, Opposition of European patent EP 2021047 B1, dated Jul. 16, 2014, on behalf of Sorbion GmbH & Co.KG, and cited publications D1-D25, in 568 pages. EP 2021047 B1 is related to the present application by virtue of a common priority claim to U.S. Appl. No. 11/432,855, now U.S. Pat. No. 7,615,036 [with references as noted within opposition].

(Continued)

*Primary Examiner* — Tatyana Zalukaeva
*Assistant Examiner* — Ilya Treyger
(74) *Attorney, Agent, or Firm* — Knobbe, Martens, Olson & Bear LLP

(57) ABSTRACT

A wound therapy device is disclosed. The wound therapy device may include a housing for covering at least a portion of a wound and for sealing to a body surface of a patient. The housing may also include a liquid collector for retaining liquid therein and a vacuum connection for coupling to a vacuum source. The vacuum connection may be in gaseous communication with the liquid collector. The vacuum connection may be separated from the liquid collector by a liquid barrier.

32 Claims, 8 Drawing Sheets

(51) Int. Cl.
  *A61F 13/00* (2006.01)
  *A61F 13/15* (2006.01)
  *B65D 69/00* (2006.01)
  *B65D 71/00* (2006.01)
  *A61M 27/00* (2006.01)

(56) References Cited

U.S. PATENT DOCUMENTS

| | | | |
|---|---|---|---|
| 5,238,732 A | 8/1993 | Krishnan | |
| 5,549,584 A | 8/1996 | Gross | |
| 5,636,643 A | 6/1997 | Argenta et al. | |
| 5,759,570 A | 6/1998 | Arnold | |
| 6,071,267 A | 6/2000 | Zamierowski | |
| 6,142,982 A * | 11/2000 | Hunt et al. | 604/313 |
| 6,156,334 A | 12/2000 | Meyer-Ingold et al. | |
| 6,626,891 B2 | 9/2003 | Ohmstede | |
| 6,685,681 B2 | 2/2004 | Lockwood et al. | |
| 6,752,794 B2 | 6/2004 | Lockwood et al. | |
| 6,936,037 B2 | 8/2005 | Bubb | |
| 6,951,553 B2 | 10/2005 | Bubb et al. | |
| 6,979,324 B2 | 12/2005 | Bybordi et al. | |
| 7,108,683 B2 | 9/2006 | Zamierowski | |
| 7,361,184 B2 | 4/2008 | Joshi | |
| 7,381,859 B2 | 6/2008 | Hunt et al. | |
| 7,569,742 B2 | 8/2009 | Haggstrom et al. | |
| 7,615,036 B2 | 11/2009 | Joshi et al. | |
| 7,625,362 B2 | 12/2009 | Boehringer | |
| 7,645,253 B2 | 1/2010 | Gura et al. | |
| 7,699,823 B2 | 4/2010 | Haggstrom et al. | |
| 7,708,724 B2 | 5/2010 | Weston | |
| 7,722,582 B2 | 5/2010 | Lina et al. | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,779,625 B2 | 8/2010 | Joshi et al. | |
| 7,811,269 B2 | 10/2010 | Boynton et al. | |
| 7,838,717 B2 | 11/2010 | Haggstrom et al. | |
| 7,846,141 B2 | 12/2010 | Weston | |
| 7,909,805 B2 | 3/2011 | Weston | |
| 7,910,791 B2 | 3/2011 | Coffey | |
| 7,922,703 B2 | 4/2011 | Riesinger | |
| 7,959,624 B2 * | 6/2011 | Riesinger | 604/543 |
| 7,964,766 B2 | 6/2011 | Blott et al. | |
| 8,062,272 B2 | 11/2011 | Weston | |
| 8,062,273 B2 | 11/2011 | Weston | |
| 8,062,331 B2 | 11/2011 | Zamierowski | |
| 8,080,702 B2 | 12/2011 | Blott et al. | |
| 8,118,794 B2 | 2/2012 | Weston | |
| 8,152,785 B2 | 4/2012 | Vitaris | |
| 8,162,907 B2 | 4/2012 | Heagle | |
| 8,207,392 B2 | 6/2012 | Haggstrom et al. | |
| 8,241,261 B2 | 8/2012 | Randolph et al. | |
| 8,282,611 B2 | 10/2012 | Weston | |
| 8,303,552 B2 | 11/2012 | Weston | |
| 8,372,049 B2 | 2/2013 | Jaeb et al. | |
| 8,372,050 B2 | 2/2013 | Jaeb et al. | |
| 8,425,478 B2 | 4/2013 | Olson | |
| 8,444,612 B2 | 5/2013 | Patel et al. | |
| 8,449,509 B2 | 5/2013 | Weston | |
| 8,460,255 B2 | 6/2013 | Joshi et al. | |
| 8,545,464 B2 | 10/2013 | Weston | |
| 8,569,566 B2 | 10/2013 | Blott et al. | |
| 8,628,505 B2 | 1/2014 | Weston | |
| 8,641,691 B2 | 2/2014 | Fink | |
| 8,715,256 B2 | 5/2014 | Greener | |
| 8,764,732 B2 | 7/2014 | Hartwell | |
| 8,795,243 B2 | 8/2014 | Weston | |
| 8,808,274 B2 | 8/2014 | Hartwell | |
| 8,829,263 B2 | 9/2014 | Haggstrom et al. | |
| 8,834,451 B2 | 9/2014 | Blott et al. | |
| 2001/0029956 A1 | 10/2001 | Argenta | |
| 2003/0040687 A1 | 2/2003 | Boynton et al. | |
| 2004/0073151 A1 | 4/2004 | Weston | |
| 2004/0241214 A1 | 12/2004 | Kirkwood et al. | |
| 2006/0009744 A1 | 1/2006 | Erdman et al. | |
| 2007/0055209 A1 | 3/2007 | Patel et al. | |
| 2007/0225663 A1 | 9/2007 | Watt et al. | |
| 2008/0306456 A1 | 12/2008 | Riesinger | |
| 2009/0227969 A1 | 9/2009 | Jaeb et al. | |
| 2009/0234306 A1 | 9/2009 | Vitaris | |
| 2009/0234309 A1 | 9/2009 | Vitaris et al. | |
| 2009/0240185 A1 | 9/2009 | Jaeb et al. | |
| 2009/0299251 A1 | 12/2009 | Buan | |
| 2009/0299306 A1 | 12/2009 | Buan | |
| 2010/0125258 A1 | 5/2010 | Coulthard et al. | |
| 2010/0160880 A1 | 6/2010 | Weston | |
| 2010/0160881 A1 | 6/2010 | Lin et al. | |
| 2010/0174251 A1 | 7/2010 | Weston | |
| 2010/0191196 A1 | 7/2010 | Heagle | |
| 2010/0191198 A1 | 7/2010 | Heagle | |
| 2010/0207768 A1 | 8/2010 | Pidgeon et al. | |
| 2010/0210986 A1 | 8/2010 | Sanders et al. | |
| 2010/0217177 A1 | 8/2010 | Cali et al. | |
| 2010/0262090 A1 | 10/2010 | Riesinger | |
| 2010/0262091 A1 | 10/2010 | Larsson | |
| 2010/0268198 A1 | 10/2010 | Buan et al. | |
| 2010/0274207 A1 | 10/2010 | Weston | |
| 2010/0305526 A1 | 12/2010 | Robinson et al. | |
| 2010/0324510 A1 | 12/2010 | Andresen et al. | |
| 2011/0004172 A1 | 1/2011 | Eckstein et al. | |
| 2011/0009838 A1 | 1/2011 | Greener | |
| 2011/0028918 A1 | 2/2011 | Hartwell | |
| 2011/0118683 A1 | 5/2011 | Weston | |
| 2011/0224631 A1 | 9/2011 | Simmons | |
| 2011/0282309 A1 | 11/2011 | Adie et al. | |
| 2012/0041399 A1 | 2/2012 | Blott et al. | |
| 2013/0110058 A1 | 5/2013 | Adie et al. | |
| 2013/0116635 A1 | 5/2013 | Fleischmann | |
| 2013/0138054 A1 | 5/2013 | Fleischmann | |
| 2013/0138060 A1 | 5/2013 | Haqqstrom et al. | |
| 2013/0144230 A1 | 6/2013 | Wu et al. | |
| 2013/0150814 A1 | 6/2013 | Buan | |
| 2013/0165878 A1 | 6/2013 | Heagle | |
| 2013/0267921 A1 | 10/2013 | Weston | |
| 2013/0274688 A1 | 10/2013 | Weston | |
| 2013/0331822 A1 | 12/2013 | Patel et al. | |
| 2013/0338613 A1 | 12/2013 | Haggstrom et al. | |
| 2014/0114263 A1 | 4/2014 | Weston | |
| 2014/0114268 A1 | 4/2014 | Auguste et al. | |
| 2014/0228791 A1 | 8/2014 | Hartwell | |
| 2014/0236109 A1 | 8/2014 | Greener | |
| 2014/0249493 A1 | 9/2014 | Hartwell | |
| 2015/0032035 A1 | 1/2015 | Banwell et al. | |

FOREIGN PATENT DOCUMENTS

| | | |
|---|---|---|
| DE | 20 2004 018 245 | 7/2005 |
| DE | 20 2004 018 245 U1 | 7/2005 |
| DE | 20 2005 019 670 | 4/2006 |
| DE | 20 2005 019 670 U1 | 4/2006 |
| EP | 1 476 217 B1 | 3/2008 |
| EP | 2 021 047 A2 | 2/2009 |
| EP | 2 462 908 A1 | 6/2012 |
| EP | 2 544 642 B1 | 1/2015 |
| EP | 2 648 668 A4 | 1/2015 |
| EP | 2 830 555 A1 | 2/2015 |
| EP | 2 836 711 A1 | 2/2015 |
| FR | 1163907 | 10/1958 |
| WO | WO 96/05873 | 2/1996 |
| WO | WO 99/01173 | 1/1999 |
| WO | WO 01/85248 | 11/2001 |
| WO | WO 01/89431 | 11/2001 |
| WO | WO 2005/025447 | 3/2005 |
| WO | WO 2005/051461 | 6/2005 |
| WO | WO 2005/123170 | 12/2005 |
| WO | WO 2006/052839 | 5/2006 |
| WO | WO 2006/056294 | 6/2006 |
| WO | WO 2007/030598 | 3/2007 |
| WO | WO 2007/030601 | 3/2007 |
| WO | WO 2007/133644 | 11/2007 |
| WO | WO 2009/124100 | 10/2009 |
| WO | WO 2009/158128 | 12/2009 |
| WO | WO 2010/142959 | 12/2010 |
| WO | WO 2010/147533 | 12/2010 |

(56) References Cited

FOREIGN PATENT DOCUMENTS

| WO | WO 2011/135285 | 11/2011 |
|----|----------------|---------|
| WO | WO 2011/135286 | 11/2011 |
| WO | WO 2011/135287 | 11/2011 |
| WO | WO 2011/144888 | 11/2011 |
| WO | WO 2012/131237 | 10/2012 |
| WO | WO 2012/140378 | 10/2012 |
| WO | WO 2012/143665 | 10/2012 |
| WO | WO 2013/010907 | 1/2013  |
| WO | WO 2013/083800 | 6/2013  |
| WO | WO 2014/008348 | 1/2014  |
| WO | WO 2014/016759 | 1/2014  |
| WO | WO 2014/108476 | 7/2014  |
| WO | WO 2014/113253 | 7/2014  |
| WO | WO 2015/022334 | 2/2015  |
| WO | WO 2015/022340 | 2/2015  |

OTHER PUBLICATIONS

English translation of Opposition of European patent EP 2021047 B1, dated Jul. 16, 2014, on behalf of Sorbion GmbH & Co., in 32 pages. EP 2021047 B1 is related to the present application by virtue of a common priority claim to U.S. Appl. No. 11/432,855, now U.S. Pat. No. 7,615,036.

Kerstin Protz, Moderne Wundauflagen unterstützen Heilungsprozess, Geriatrie Journal, Apr. 2005, pp. 3333-3339, Germany.

"Kendall ULTEC Hydrocolloid Dressing (4"×4")(Box of 5)", www.metromedicalonline.com/8884475400.html, printed Jul. 13, 2014, 1 page.

English Translation of Invalidity Suit by KCI Medizinprodukte GmbH versus Kalypto Medical, Inc., concerning declaration of invalidity of the German part of the European Patent No. 2 021 046 (German application No. 60 2007 021 330.4) dated Mar. 11, 2015 in 38 pages. EP 2 021 046 is related to the present application by virtue of a common priority claim to U.S. Appl. No. 11/432,855, now U.S. Pat. No. 7,615,036, and U.S. Appl. No. 11/610,458, now U.S. Pat. No. 7,779,625.

Response to Communication of Notice of Opposition dated Mar. 24, 2015 re European Patent No. 2 021 047 in 24 pages.

Clean Auxiliary Requests as filed on Mar. 24, 2015 re European Patent No. 2 021 047 in 45 pages.

Marked-up Auxiliary Requests as filed on Mar. 24, 2015 re European Patent No. 2 021 047 in 45 pages.

Appendix PA1 Hydrokolloide Verbände http:--www.pflegewiki.de-wiki-Hydrokolloide_Verbände dated Jan. 19, 2015 in 3 pages. English translation produced using Google translate on May 26, 2015.

Protz, Kerstin: English translation of "Modern Wundauflagen unterstutzen Heilungsprozess", Wundversorgung: Indikation und Anwendung, Geriatrie Journal Apr. 2005, pp. 3333-3339.

* cited by examiner

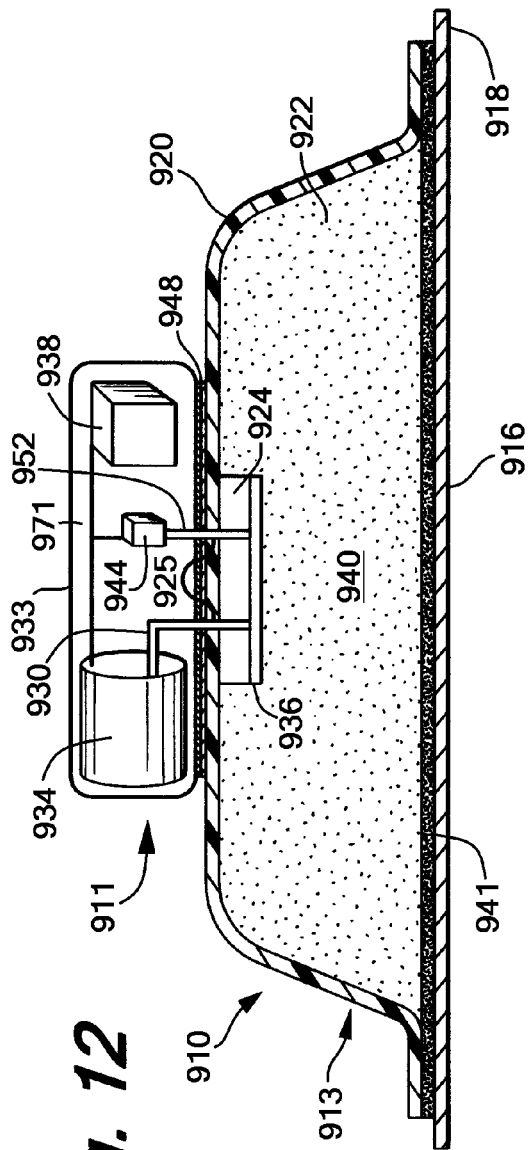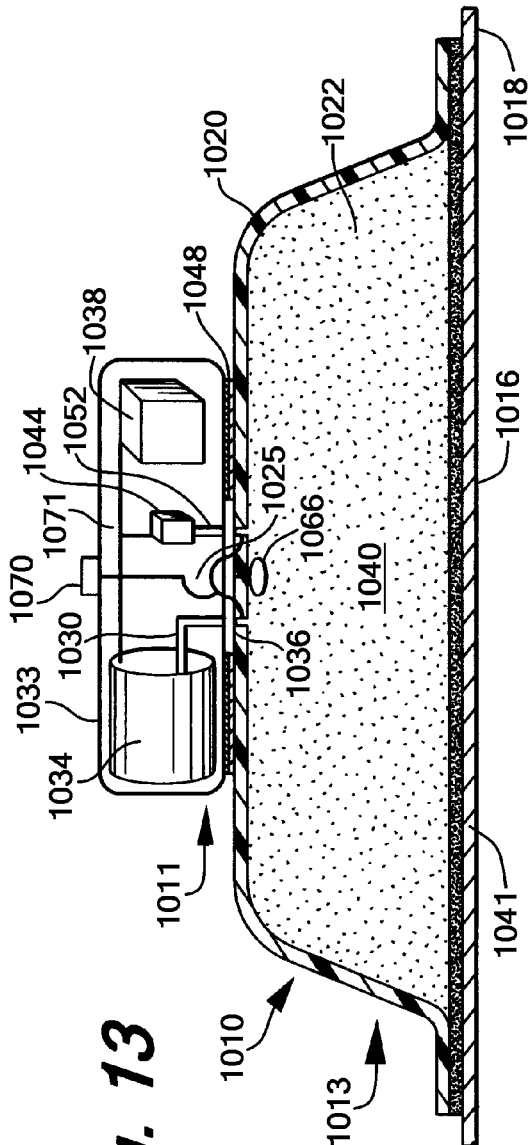

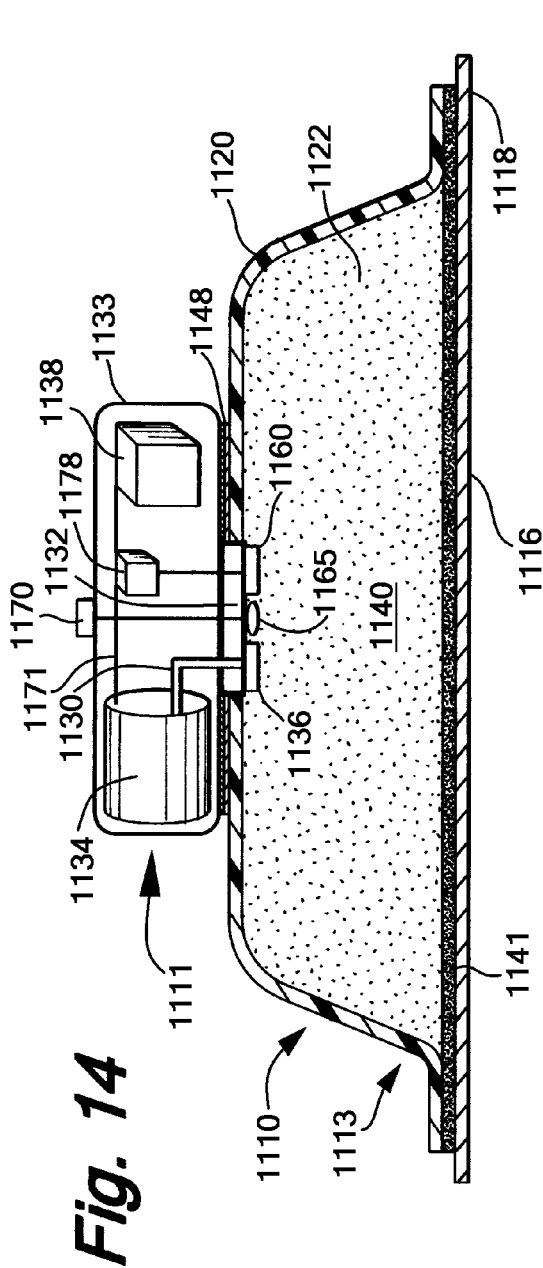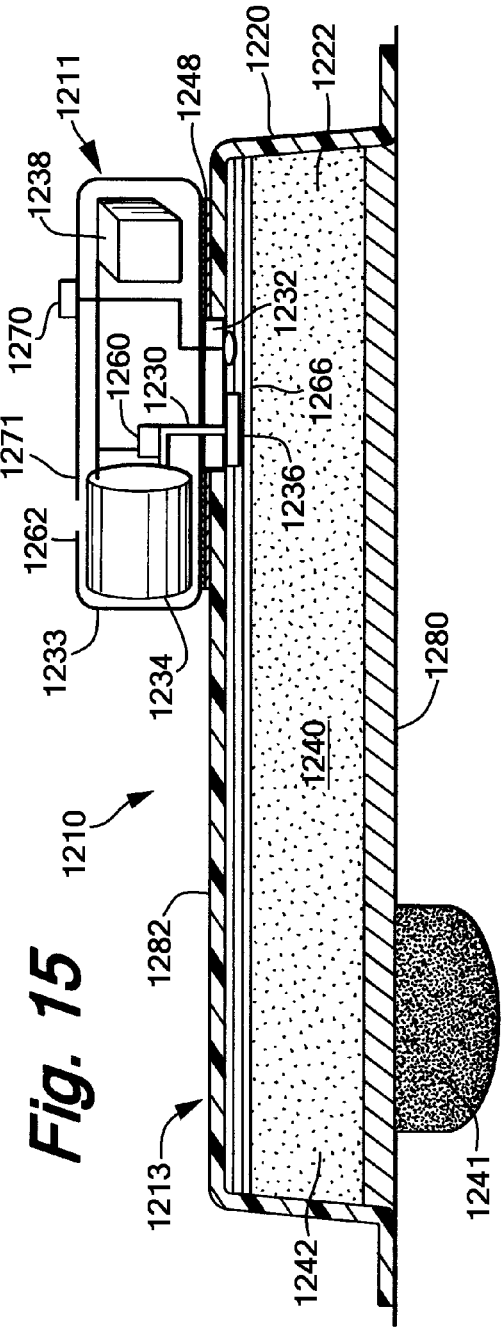

DEVICE AND METHOD FOR WOUND THERAPY

RELATED APPLICATIONS

This application is a continuation application of pending U.S. patent application Ser. No. 12/592,049, filed Nov. 18, 2009, which is a divisional application of U.S. patent application Ser. No. 11/610,458, filed Dec. 13, 2006 (now U.S. Pat. No. 7,779,625), which is a continuation-in-part of, and claims priority to, U.S. patent application Ser. No. 11/432,855, filed on May 11, 2006 (now U.S. Pat. No. 7,615,036), all of which are incorporated herein by reference.

TECHNICAL FIELD

The disclosure relates in general to a device and method for wound therapy that is capable of treating a variety of chronic and acute wound types, including, but not limited to, infection wounds, venous ulcers, arterial ulcers, diabetic ulcers, burn wounds, post amputation wounds, surgical wounds, and the like. Specifically, the present disclosure is related to wound treatment devices and methods that utilize negative pressure therapy.

BACKGROUND

Negative pressure therapy has been one tool used for the treatment of a variety of wounds by practitioners in the art. Conventional devices are generally large in size and often require the use of complicated equipment such as suction pumps, vacuum pumps and complex electronic controllers. Other associated equipment may include wound liquid/exudate collection canisters, liquid transporting conduits, and pressure regulators/transducers/sensors. As a result, such devices may be bulky, power intensive, relatively costly and substantially non-disposable. Furthermore, the complexity of conventional devices requires steady patient supervision and that initial placement and any changing of the devices be conducted by a physician or nurse. At present, a typical cost for the use of these devices is on the order of about $100 per day per patient.

The rising costs of healthcare and of medical devices place pressure on patients and care providers alike to seek out solutions that allow use by a patient in-home, with less supervision. Furthermore, patients continue to demand devices that are more easily portable to allow travel and mobility.

BRIEF SUMMARY

The present disclosure provides a self-integrated wound therapy device for providing negative pressure therapy to a wound. In one embodiment, the device may include a housing to cover at least a portion of a wound. The device may also include a liquid collector within a liquid retention chamber and an adaptor or coupling for coupling to a vacuum source. The vacuum connection may be in gaseous communication with the liquid-retention chamber. The vacuum connection may be separated from the liquid collector by a liquid barrier. The wound therapy device may also include a seal to seal the housing to a body surface of a patient.

The vacuum connection in some embodiments may be coupled to a vacuum source that may be optionally located within or adjacent to the housing. In other embodiments, the vacuum connection may comprise an adapter that may be coupled to a vacuum source located external to the housing. As used throughout this specification, adapter and coupler or coupling may be used interchangeably.

In other embodiments, the wound therapy device may be modular in nature, optionally including a wound interface module, a retention module and a vacuum source module. Each module of the wound therapy device may be optionally replaceable individually or in combination.

BRIEF DESCRIPTION OF THE SEVERAL VIEWS OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings as provided below.

FIG. 12 is a side cross-sectional view of another embodiment of a wound healing device.

FIG. 13 is a side cross-sectional view of another embodiment of a wound healing device.

FIG. 14 is a side cross-sectional view of another embodiment of a wound healing device.

FIG. 15 is a side cross-sectional view of another embodiment of a wound healing.

DETAILED DESCRIPTION

Figure 1:
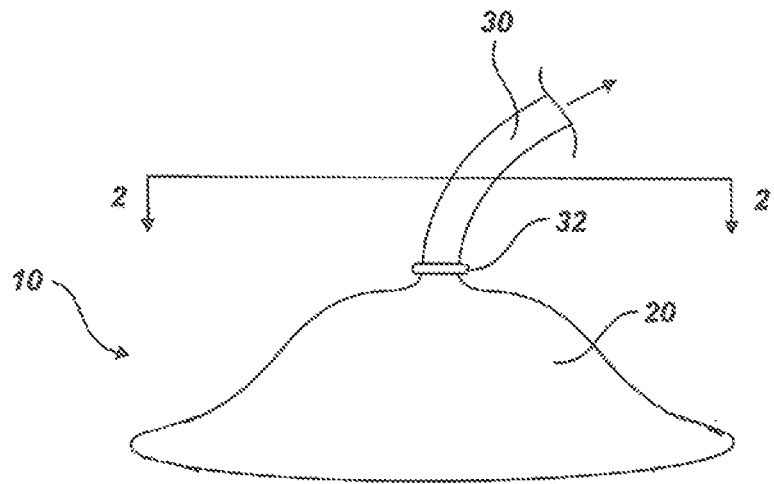
FIG. 1 is a perspective view of one embodiment of a wound healing device.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In the following description, numerous specific details are provided, such as examples of housings, barriers, chambers etc., to provide a thorough understanding of embodiments of the invention. One skilled in the relevant art will recognize, however, that the invention can be practiced without one or more of the specific details, or with other methods, components, materials, and so forth. In other instances, well-known structures, materials, or operations such as vacuum sources are not shown or described in detail to avoid obscuring aspects of the invention.

Figure 2:
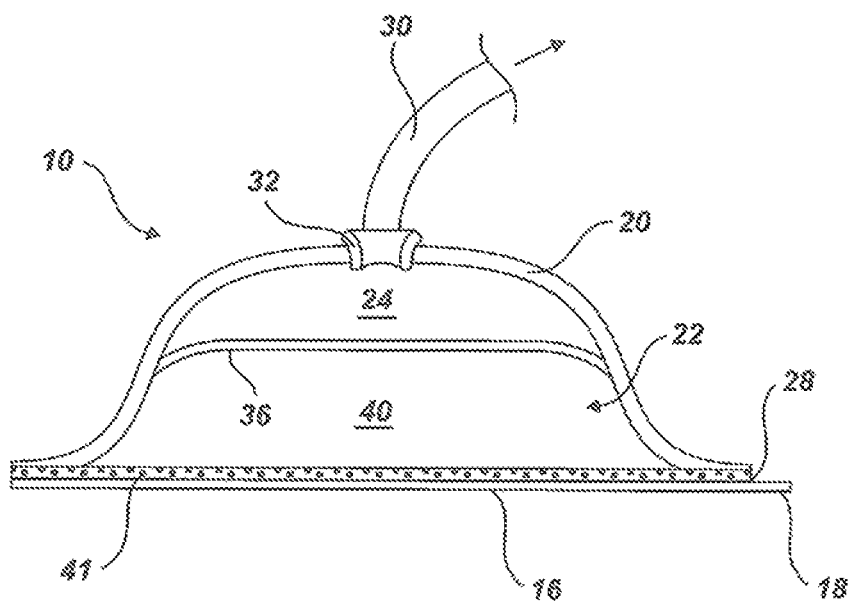
FIG. 2 is a side cross-sectional view of the wound healing device of FIG. 1.

Referring now to FIGS. 1 and 2, a wound therapy device 10 is shown. FIG. 1 shows a wound therapy device shown in a perspective view as would be attached to a body surface of a patient for at least partially encompassing a wound. FIG. 2 shows a side cross-sectional view of the device of FIG. 1 taken along plane 2-2 of FIG. 1. The device 10 includes a housing 20 configured to cover at least a portion of a wound. The housing 20 defines an internal space 22. In one embodiment, the internal space 22 may contain a vacuum chamber 24 and a liquid-retention chamber 40 separated by a liquid barrier 36. The liquid-retention chamber 40 may include a liquid collector (not shown) for collecting wound exudate or other liquid. The housing is configured to be in fluid communication with a vacuum source (not shown). The liquid collector retains wound exudate while simultaneously communicating negative pressure generated by the vacuum source to the wound. As used throughout this specification, negative pressure and vacuum may be used interchangeably.

In one embodiment the housing 20 is rigid or semi-rigid. The housing 20 of the device 10 substantially retains its size and structure during the application of negative pressure, thus allowing a vacuum to be held within the housing 20. The housing 20 may be produced out of any suitable material known to one of ordinary skill in the art, including, without limitation, rubbers, including polyurethane, and dense plastics such as, but not limited to, polypropylene, polyvinyl chlorides, polyethylene, acrylonitrile-based copolymer, such as those sold under the Barex® brand, polyester, polystyrene, polyether, nylon, polychlorotrifluoroethylene, fluoropolymer, polytetrafluoroethylene, such as those sold under the Teflon® brand, silicone, neoprene or combinations thereof and similar materials.

In another embodiment, the housing 20 is made of a flexible barrier or a surface wrap supported by at least one customizable rigid or semi-rigid structural support (not shown) present within the internal space 22 of the housing to maintain the shape of the device when the device is subjected to pressure lower than atmospheric pressure. In some embodiments, the structural supports may be external to the housing or integral with the housing 20. The flexible barrier or surface wrap may be a thin polyurethane film with a dermal compatible adhesive supported by structural foam present within the internal space 22 of the housing 20. The structural supports or structural foam can be made from rigid or semi-rigid plastics and foams, e.g., polystyrene, polyester, polyether, polyethylene, silicone, neoprene, combinations thereof, and the like. Alternatively, the liquid-retention chamber 40 or a liquid collector positioned therein may by itself provide the needed structural support to maintain vacuum passages within the housing 20 open upon application of vacuum.

In one embodiment, the housing 20 is semi-permeable. An exemplary semi-permeable housing 20 may be substantially impermeable to liquids but somewhat permeable to water vapor and other gases while capable of maintaining a negative pressure underneath the housing 20 upon application of a vacuum. By way of example, the housing 20 material may be constructed of polyurethane or other semi-permeable material such as those sold under the Tegaderm® brand. In one embodiment the housing 20 may have a water vapor transmission rate ("WVTR") of about 836 grams/m$^2$/day or more. However, in other embodiments the WVTR may be less than about 836 grams/m$^2$/day. In yet other embodiments, the housing 20 material may be substantially impermeable to both liquids and gases (including water vapor). Other exemplary housing materials may include materials sold under the Opsite®, Suresite®, Medfix®, and Mefilm® brand names.

The device may be made of material to make it conformable for use with wounds in various locations. For example, the wound may be on an elbow or other joint such the device may need to be conformed to make a good seal around the wound site.

The vacuum source (not shown) is in fluid communication with the housing 20. A vacuum connection 30 may connect the housing 20 and the vacuum source. The vacuum connection may include without limitation, flexible or semi-rigid medical tubing known in the art, a plenum, a conduit, or other passage capable of transmitting the vacuum from the vacuum source to the housing 20. In one embodiment, the housing is fitted with an adaptor 32 or coupling 32 that allows the housing 20 to be attached to the vacuum connection 30 or to an external vacuum source. The vacuum source may be located internal to or external to the housing 20 and may be remote or adjacent to the housing. Where the vacuum source is external to the housing 20 and adjacent the housing 20, the vacuum connection 30 may not be necessary and the vacuum may be communicated to the housing 20 directly from the vacuum source through the adapter 32 or coupling 32. In embodiments, wherein the vacuum source is within the housing 20, the adapter 32 or coupling 32 may not be needed. The vacuum source may be a micro-vacuum pump or a regular vacuum pump. The pumps may be of any kind known to those skilled in the art. The vacuum source may also be an osmotic or electroosmotic pump.

The vacuum source may include and operably be coupled to a power source or supply, such as a battery. Power sources referred to herein may be, for example, electrical outlets, batteries, and/or rechargeable batteries and the like. The batteries may be integral (non-replaceable), replaceable and/or rechargeable. The power source may be located adjacent to the vacuum source or may be positioned remotely so that a larger capacity power source that could last for the duration of the treatment can be used.

The adapter 32 or coupling 32 can simply be a vacuum port for connecting an outlet of the vacuum source. The adapter 32 or coupling 32 can also be configured to provide more complex communication between the housing 20 and the vacuum source. The adapter 32 or coupling 32 may be fitted to carry communication channels and/or lines between a control module in the vacuum source or vacuum source module and sensors positioned within the interior of the housing 20.

In one embodiment, the adapter 32 or coupling 30 is in gaseous communication with the vacuum chamber 24, which in turn is in communication with the liquid-retention chamber 40 via the liquid barrier 36. In an alternative embodiment, the vacuum connection 30 is directly in communication with the liquid-retention chamber 40 via the liquid barrier 36. In another alternative embodiment, the outlet of the vacuum source is directly connected to the liquid barrier. The vacuum source, the vacuum 30 connection and the vacuum chamber 24 and the liquid barrier 36 may all be external or internal to the housing.

The adapter 32 or coupling 32 may be a design feature associated with the housing 20 or vacuum source to allow the housing 20 and vacuum source to be coupled together. This coupling may be accomplished by interference fit, snap fit, compression fit, and the like. The adapter 32 or coupling 32 may also be accomplished by adhesion or a by mechanical device as is known in the art to provide a coupling for maintaining the vacuum source in communication with the housing. The adapter 32 or coupling 32 is configured to transfer negative pressure generated by the vacuum source to the housing 20.

The vacuum chamber 24 of the embodiment of device 10 illustrated in FIG. 1 is defined by the interior of the housing 20. The vacuum chamber 24 may be an empty space or may be filled with a porous material that allows communication of the vacuum. The vacuum chamber 24 establishes a positive connection for the vacuum force or pressure that enhances the distribution or transfer of the vacuum pressure to the liquid collector. The vacuum chamber 24 may also serve to distribute the vacuum pressure more evenly to the liquid collector. It will be appreciated by those of skill in the art that the vacuum chamber need not be defined by the housing 20, but may also be outside the housing. For example, the vacuum chamber 40 may be the conduit in the vacuum connection 30. The vacuum chamber 40 may also be within space defined by the adapter 32.

The liquid collector includes at least one porous material that includes a plurality of passages to allow fluid communication between the vacuum source and the wound through the liquid collector. The liquid collector may include structures and/or substances to assist in retaining the liquids drawn from the wound. Such structures and/or substances may include sponges, foams, fibers, wicking fibers, hollow fibers, beads, fabrics, or gauzes, super-absorbent materials including super-absorbent polymers in various forms, absorbent foams, gelling agents such as sodium carboxy methyl cellulose, packing materials, and combinations thereof. Such structures or substances have passages that permit the flow of gas and allow the vacuum or negative pressure to be applied to the wound. These structures or substances also absorb and retain liquid drawn out of the wound. It will be appreciated by those of skill in the art that liquid in the form of wound exudate may include solid components such as cellular debris and other solids that are typically found in wound exudates.

The materials or structures that make up the liquid collector form or contain interstitial spaces that serve as negative pressure passageways. These allow the vacuum source to be in fluid communication with the wound through the liquid collector. In one embodiment, the liquid collector may be a composite structure of fibers made of polyester or rayon with superabsorber fibers made of sodium polyacrylate among others dispersed throughout the structure to form a fiber matrix. The superabsorber fibers or particles are distributed discretely within the fiber matrix such that the gas (vacuum) passage ways are open even after substantial liquid uptake by the superabsorber fibers or particles. The superabsorber fibers may act as, or contain, nodes within the liquid collector. As liquid is absorbed by the liquid collector, the liquid collects at the super absorber nodes without blocking the gas (vacuum) passageways within the liquid collector. In another embodiment, the wound exudates that enter the liquid collector are absorbed by the superabsorber material and are immobilized at discrete locations within the fiber matrix or other liquid collector material. Thus, the liquid collector retains the liquid during the application of vacuum as well as when the vacuum is off.

In another embodiment, the liquid collector has areas or zones that are prevented from becoming saturated or super saturated. In these embodiments, the non saturated zones or areas make up the passages for communication vacuum or negative pressure from the vacuum source through the liquid collector to the wound. Accordingly, the device 10 includes means for maintaining a therapeutic pressure at the wound while the liquid collector is absorbing liquid.

In one embodiment, the liquid collector, housing 30, and/or liquid retention chamber 40 is sufficiently rigid to allow fluid communication between the vacuum source and the wound through the liquid collector when the device is subject to a pressure lower than atmospheric pressure. The device 10 has sufficient rigidity or structure so that the passages through the liquid collector will remain open under vacuum pressure, thus allowing vacuum or negative pressure to be transmitted to the wound.

The liquid collector is configured to retain liquid under a predetermined amount of mechanical force applied to the liquid collector. For example, the liquid collector may retain liquid even when the device 10 is squeezed by a user. This feature prevents oozing of free liquid from the liquid collector when the vacuum source is off or when the retention chamber or liquid collector needs to be replaced.

In one embodiment, the liquid collector is a composite structure made of a structural fiber matrix with superabsorber fibers dispersed within. Such a structure maintains sufficient structural integrity under the application of vacuum to keep vacuum passages open. Hence no additional structural supports are needed.

Other means for collecting and retaining liquid having similar features that are known to one of ordinary skill in the art may also be used. In some embodiments, the liquid collector or the liquid-retention chamber 40 may be antimicrobial in nature or may include antimicrobial agents.

The liquid collector may be within the liquid-retention chamber 40, or may be part of the structure that defines the liquid-retention chamber 40. As used herein, "retaining liquid" or "the retention of liquid" means substantially retaining the liquid. In some embodiments, the liquid-retention chamber itself can provide the needed structural support to maintain vacuum passages within or through the housing open upon application of vacuum. Thus, the device has sufficient structure to maintain the functionality of the device under application of a vacuum. As will be discussed in greater detail below, a fill indicator may alert the user at a predetermined liquid collector saturation point.

The liquid barrier 36, in one embodiment, is positioned between the vacuum source and the liquid collector (not shown). The liquid barrier 36 serves to prevent travel of liquid from the liquid-retention chamber 40 to the vacuum chamber 24. The liquid barrier 36 may also be a gas permeable membrane. As such, it may comprise any of a large family of suitable technologies that prevent travel of liquid from the liquid-retention chamber 40 into the vacuum chamber 24 while allowing gas flow, and thus transmission of negative pressure provided through the vacuum connection 30. It will be appreciated by those of skill in the art that the liquid barrier 36 may be in the form of a film, a mat, a membrane or other structure that is liquid impermeable. For example, the liquid barrier 36 may include a porous hydrophobic film, a porous hydrophobic membrane, or other hydrophobic structure, or other ways to preclude moisture travel.

Examples of porous hydrophobic films include, but are not limited to, porous and microporous polytetrafluoroethylene, polypropylene, polyvinylidene difluoride, acrylic polymers, polyethylene, or fibrous layers of each and combinations thereof. For example, porous hydrophobic films sold under the Gore-Tex® or Millipore® brands may be suitable. These hydrophobic films may also act as anti-microbial filters and prevent passage of bacteria from the liquid-retention chamber to the vacuum source and vice versa. Other technologies that allow gas flow but prevent liquid flow may also be used as suitable liquid barriers 36 as would be apparent to those having skill in the art with the aid of the present disclosure.

In the device 10 of FIG. 2, the liquid barrier 36 is a porous hydrophobic film configured to allow gas flow while at least substantially blocking liquid flow. Thus, when a vacuum source (not shown) is attached to the means of communicating the vacuum, which in the illustrated embodiment is the adapter 32 of the vacuum connection 30, negative pressure is supplied/transmitted through the vacuum chamber 24 into the retention chamber 40, drawing liquid from the wound site into the liquid-retention chamber 40.

In one embodiment, the wound therapy device 10 includes means for maintaining operation of the device independent of device orientation. For example the device may need to be located at various locations on the patient's body and must function at different angles including when the device is completely inverted. In one embodiment, the means for maintaining the functionality of the device independent of device orientation includes the liquid barrier 36 which keeps moisture out of the vacuum source regardless of device orientation. The means also includes the individual components of the device which are designed to be orientation independent. The means for maintaining the device operation independent of the device orientation may include the liquid collector being fabricated from a material which gels and immobilizes the wound exudates thereby preventing clogging of vacuum passageways by the free liquid. For example, where the liquid collector includes a fibrous matrix with supper absorber nodes dispersed throughout the matrix, the exudate may gel at the nodes removing the liquid while continually providing vacuum passageways.

The device 10 may additionally contain a wound interface 41 in direct contact with the wound and may comprise single or multiple layers of varying thicknesses to accommodate the depth of the wound. The wound interface 41 may be either placed directly inside the wound or over the wound. The wound interface 41 is in fluid communication with the liquid-retention chamber and is configured to transfer wound fluid from a wound bed to the liquid-retention chamber 40. In one embodiment, the wound interface 41 transfers fluid by wicking action. In another embodiment, the wound interface 41 transfers fluid by capillary action. The wound interface 41 may be porous to allow wound fluid to pass through for absorption by the overlying liquid collector. Alternatively, the wound interface 41 may partially or fully absorb wound fluids. The wound interface 41 may be a sheet, a foam, a gel, a gauze, a porous matrix, a honeycomb, a mop, confetti, and combinations thereof.

The wound interface 41 may be either placed directly inside the wound or over the wound. The wound interface 41 may serve many functions such as being a layer that allows supply of vacuum to the wound while allowing easy and painless removal from the wound site of the liquid-retention chamber 40 after it reaches a predetermined absorption level. The wound interface 41 may be degradable copolymer foil, such as those sold under the Topkin® brand, or a layer that provides beneficial bioagents in the form of specialized dressings such as dermal regeneration templates (e.g., those sold under the Integra® brand), bioabsorbable gels, foams and barriers that prevent tissue adhesion (e.g., those sold under the Incert® brand), a skin substitute (e.g., those sold under the BioFill® brand), a layer for selectively maintaining moisture at the wound site (e.g., alginates or dressings such as those sold under the Alevyn® brand), a layer that is angiogenic (e.g., those sold under the Theramers brand), and/or a layer that is antimicrobial or includes an antimicrobial agent.

The wound interface 41 may take a variety of forms including but not limited to a sheet, foam, gel, gauze or other space filling porous structures such as a pouch of beads, a shaggy mop, loose confetti or a honey comb. Alternatively, the wound interface 41 can be a gel that fills the wound cavity, which turns into a porous structure on application of the vacuum. In one embodiment, the wound therapy device includes a surface in contact with the wound having at least one pore larger than about 100 microns in diameter.

It will be appreciated by those of skill in the art that the wound interface 41 and liquid collector may be combined in a variety of ways to accomplish the teachings of the invention. For example, the wound interface 41 and liquid collector may be separate layers of an integral body. In one embodiment, a plurality of the liquid collectors may each be enclosed within a pouch that acts as the wound interface. The cover of the pouch is fabricated from the wound interface formed from a porous material that is permeable to vacuum and body fluids. Liquid collector material is enclosed within this porous pouch. In one embodiment the wound interface prevents direct contact between the liquid collector material and the wound. However, it is contemplated that in some embodiments there may be some contact. This wound interface/liquid retention combination can take many forms including pillows, tubes, self-contained tubular structures and similar structures where the liquid collector can be enveloped in the wound interface. These structures are flexible and can be formed into a suitable shape to fit any kind of wound cavity. Alternatively, several of these pouches can be linked together or otherwise combined to form structures that can be inserted into a deep wound tunnel or deep wound cavity. For example, a linked tubular chain can be formed that can be inserted within a wound tunnel such that the entire wound cavity is filled with this chained structure. A flexible barrier housing material such as Tegaderm can then be used to cover the wound site and seal on the skin around the wound site. The module containing the vacuum source is attached to the flexible barrier housing to create vacuum within the wound cavity. Wound exudate enters the inside of the pouch through the permeable outer wound interface cover and gets absorbed within the liquid collector. As before, the liquid collector will permit application of vacuum to the wound while absorbing and retaining liquid drawn out of the wound.

As will be discussed in greater detail below, the device 10 may include a skin protection layer. The skin protection layer may protect the healthy skin around the wound from bruising or maceration due to undesirable exposure of the healthy skin to vacuum and moisture during wound therapy. Such a skin protection layer will allow the healthy skin to "breathe" and also allows easy and painless removal of the device from the wound site. The skin protection layer may be sealed separately to the skin first and the housing may be then sealed to the skin protection layer. Alternatively, the skin protection layer may be integral to the housing or the wound interface. The skin protection layer may be the same as the housing material or may be a gel.

When the device 10 is placed on a patient and activated, or attached to an external vacuum source via a vacuum connection 30 or simply through an adapter 32, the device 10 delivers negative pressure to the wound. The device 10 is generally attached to the body surface of a patient using one of a variety of seals known in the art, such as, in one embodiment, a housing seal 28. The housing 20 of the device 10 may be adapted to be sealed to a body surface of a patient. In some embodiments, this sealing may occur simply as a result of placing the housing 20 against the body surface and drawing a vacuum within the device 10. The device 10 may include a seal 28 for attaching the device to a surface. Adhesives, gaskets, and other seals or sealing technologies known to one of ordinary skill in the art may also be used as a seal 28 including the use of adhesive backed thin polyurethane films. Other suitable seals are known to those of ordinary skill in the art and may be used with the embodiments disclosed. In one embodiment, the device includes a leak detector in operable communication with the seal to determine whether vacuum or negative pressure is escaping from the device 10 out the seal 28.

In one embodiment, the seal 28 may be part of housing 20 or may be integral with the skin protection layer. It will be appreciated by those of skill in the art that the seal 28, housing 20 and skin protection layer may be combined in a variety of different ways to accomplish the teachings of this invention.

Thus, in operation, the device 10 may be applied to a wound site of a patient like a patch, wherein a vacuum source coupled to the vacuum connection 30, provides negative pressure to the wound. Prior to use, the device 10 may be packaged to prevent contamination. Such packaging could be a bag or envelope, or could include the use of an optional protective cover 16, with an optional pull tab 18 that is removed from the device prior to placement on the patient. During application of negative pressure to the wound site, liquid is drawn into the liquid-retention chamber 40 and held within the liquid-retention chamber 40, being prevented from further travel by the liquid barrier 36.

Figure 3:
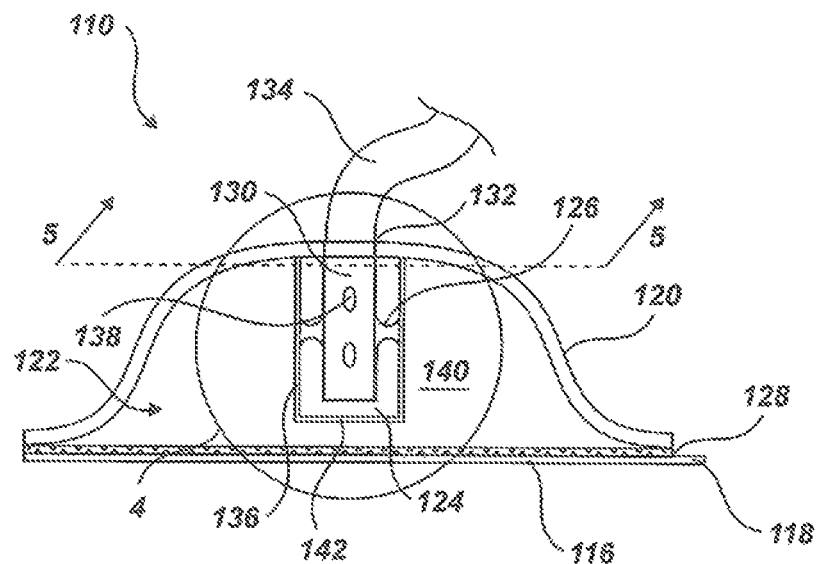
FIG. 3 is a side cross-sectional view of another embodiment of a wound healing device including a droplet gap as a liquid barrier.

Referring now to FIG. 3, another embodiment of a wound therapy device 110 is shown from a side cross-sectional view analogous to that of FIG. 2. The wound therapy device 110 of FIG. 3 includes a housing 120 and a vacuum passage 130. In the device 110 of FIG. 3, the vacuum passage 130 is a port 132 adapted to receive an external vacuum source through a vacuum connection 134 in a sealed manner, such that the vacuum source may apply a negative pressure to the device 110. In alternative embodiments, the vacuum source may be adjacent to and internal or external to the housing 120. In an exemplary device 110, the vacuum source not shown may be shared between a series of devices 110 on a single patient, or between several patients since no liquid passes into the respective vacuum connections 134 by the respective devices 110. As with the device 10 of FIGS. 1 and 2, the wound therapy device 110 of FIG. 3 may include a liquid-retention chamber 140 and a vacuum chamber 124. In this embodiment, the vacuum chamber 124 itself serves as a liquid barrier 136, acting as a "droplet gap" unable to be traversed by liquids drawn into the liquid-retention chamber 140. The "droplet gap" refers to the gap between the liquid retention chamber 140 and the vacuum passage 130. The surface tension of the liquid present in the liquid retention chamber prevents droplets from jumping the "droplet gap" to the vacuum passage. Therefore the "droplet gap" acts as a liquid barrier to prevent liquid from leaving the liquid retention chamber 140.

More specifically, the vacuum chamber 124 may be a cylindrically-shaped void within the internal space 122 of the housing 120, which, due to its size, prevents liquid from traveling from the liquid-retention chamber 140 into the vacuum passage 130. The vacuum passage 130 may extend into the vacuum chamber 124, and may include at least one orifice 138. The housing 120 may also include internal supports 126 that extend between the vacuum passage 130 and the perimeter 142 of the liquid-retention chamber 140 to maintain proper distance between the vacuum passage 130 and the liquid-retention chamber 140.

A labyrinth may also be used as a liquid barrier to prevent liquid from leaving the liquid retention chamber 140. The labyrinth approach utilizes the principle of coalescence and employs structures used in commercially available mist eliminators as are well understood by chemical engineers. Liquid or mist that enters the labyrinth will coalesce and will be redirected back to the liquid retention chamber without entering the vacuum passage 130.

The wound therapy device of FIGS. 1 and 2 could be modified to take advantage of the droplet gap principle illustrated in FIG. 3 simply by omitting the liquid barrier 36. The droplet gap or labyrinth means may also be effectively used instead of a hydrophobic liquid-barrier for maintaining a vacuum within the device independent of device orientation.

Referring again to FIG. 3, the device 110 may optionally include a liquid barrier 136 in the form of a porous hydrophobic membrane positioned between the liquid retention chamber 140 and the vacuum chamber 124.

Figures 4, 5:
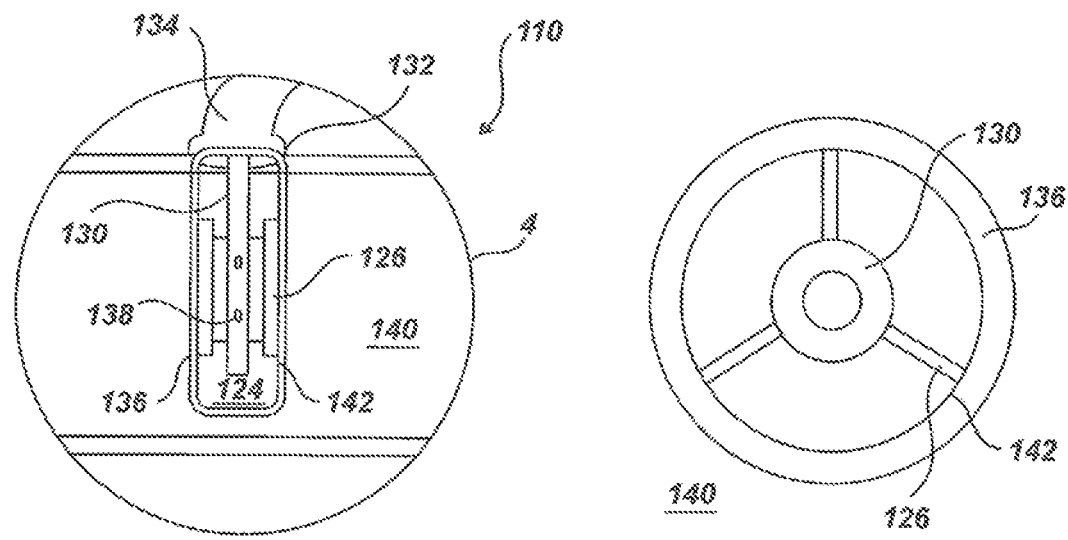
FIG. 4 is a magnified view of the droplet gap of the device of FIG. 3.
FIG. 5 is a top cross-sectional view of the droplet gap of the device of FIG. 3.

FIG. 4 is a detail view of the vacuum chamber 124 and liquid barrier 136 of the device 110 of FIG. 3 showing the contents of circle 4 of FIG. 3. As depicted, internal supports 126 structurally locate the vacuum passage 130 within the vacuum chamber 124.

The exemplary structure, shape, and construction of the vacuum chamber 124 of the device 110 is further illustrated in FIG. 5, which is a cross-sectional view of the wound therapy device 110 of FIGS. 3 and 4 taken along plane 5-5 of FIG. 3. Internal supports 126 extend between the vacuum passage 130 and the perimeter 142 to maintain proper distance between the vacuum passage 130 and the liquid-retention chamber 140. In FIG. 5, the vacuum chamber 124 is illustrated to have a cylindrical profile. It should be noted that variation of the size, volume, or shape of the vacuum chamber 124 is within the skill of one of ordinary skill in the art. Thus, elliptical, rectangular, and other shapes, without limitation, are considered to be within the scope of the present disclosure.

The liquid barriers and/or vacuum chamber configurations described above include passages that form part of the passage between the vacuum source and the wound that carries the negative pressure to the wound. Accordingly, these configurations form part of the means for communicating a vacuum between the vacuum source and the wound.

Figure 6:
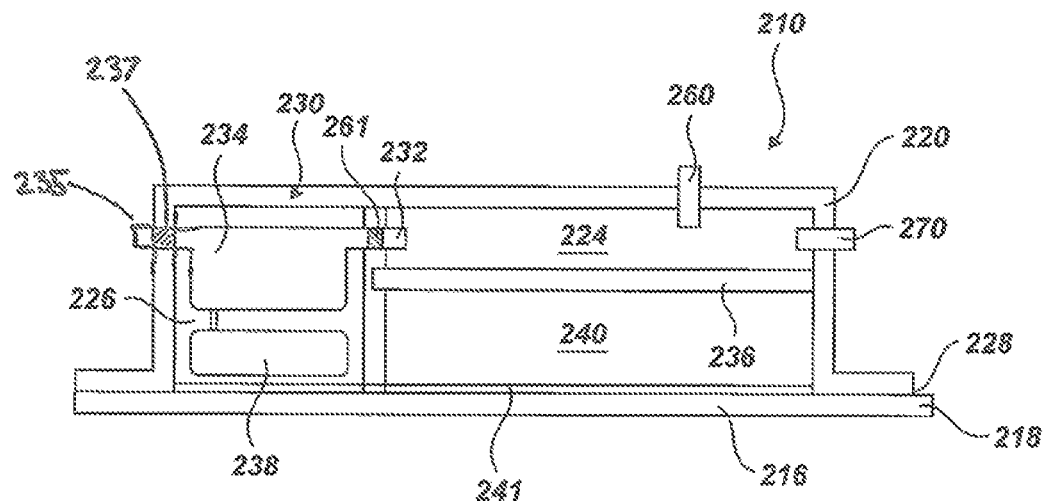
FIG. 6 is a side cross-sectional view of another embodiment of a wound healing device including an internal vacuum pump as the vacuum source.

Referring next to FIG. 6, another embodiment of the wound therapy device 210 is shown in a side cross-sectional view analogous to that of FIG. 2. The device 210 of FIG. 6, like those previously illustrated, includes a housing 220 that encloses an internal space. This embodiment of the wound therapy device 210, however, is configured to include a negative pressure source 230, including a vacuum source 234 and an adaptor 232 that supplies negative pressure to the vacuum chamber 224. The vacuum source 234 is operably coupled to a power source 238 which together may be internal to the device 210 as illustrated. Further, although the vacuum source 234 and power source 238 are illustrated to be internal to the housing 220, in an auxiliary chamber 226 in FIG. 6, it should be understood that such apparatus may be located outside of the housing 220, or may alternatively be placed in a modular portion of the device 210 which may be removed and replaced as needed.

In some embodiments, negative pressure may be applied to the liquid-retention chamber 240 and/or liquid collector via a tube or other coupling 232 or adapter 232 attached to the vacuum pump 234. When the vacuum source 230 is an internally-placed vacuum pump 234, the coupling 232 may travel from the pump 234 to the vacuum chamber 224 in gaseous communication with the liquid-retention chamber 240. When the vacuum source 230 is an internally-placed vacuum pump 234, an outlet 235 is provided for the vacuum pump or other vacuum source to vent. The outlet may include a filter 237 to prevent germs from outside from entering inside or vice-versa. The opening of the coupling 232 in the vacuum chamber 224 may include a filter 261 or can have similar properties to the liquid barrier 236 (such as, in some embodiments, as an antimicrobial filter) to prevent wound liquids from reaching the vacuum source 230 and to prevent any outside germs from entering the wound site. Moreover, in some embodiments the device 210 may include both inlet and outlet filters to prevent venting of microorganisms outside the housing 220.

In operation, the wound therapy device 210 may first be placed on a body surface of a patient so as to at least partially enclose a wound area. As discussed above, the device 210 may be sealed to the body surface using either just the suction generated by the device 210 alone, or using a seal 228 chosen from those known to those skilled in the art. The seal 228 illustrated in FIG. 6 is an adhesive seal covered during storage by a cover 216, optionally including a pull tab 218. The device 210 may further include a wound interface 241 as described herein.

Following attachment of the device 210 to a patient, the vacuum source 234 is activated, reducing the internal pressure of the device 210. As negative pressure is generated, liquids are drawn from the wound into the liquid-retention chamber 240 of the device 210, and are blocked from further progress into the vacuum chamber 224 or the negative pressure source 230 by the liquid barrier 236. As in the previous embodiments, the liquid barrier 236 may be any of those known to those of ordinary skill in the art, including, without limitation, porous hydrophobic films, membranes, and porous hydrophobic structures such as sponges and/or foams.

The exemplary device 210 of FIG. 6 may further comprise a pressure relief valve 260, a fill indicator 270, and a non-seal indicator (not shown). In some specific embodiments, the housing 220 may further include means for controlling pressure within the housing. The means for controlling pressure may include without limitation, a pressure relief valve or a pressure control valve or other pressure controller. The pressure relief valve 260 may be used to maintain negative pressure within the internal space of the housing 220 (and thus within the liquid-retention chamber 240 and at the wound surface) at a therapeutic value. Pressure relief valves may be any of the kind commercially available. In one embodiment, the negative pressure is maintained between about 75 mm Hg to about 125 mm Hg. The pressure relief valve can be located anywhere on the device where the vacuum is established. In one embodiment, the pressure relief valve 260 is located on the housing 220 so that it can respond to changes in the liquid-retention chamber 240. The pressure relief valve 260 may also be located on the vacuum source itself or in between the housing and the vacuum source 230. The pressure relief valve 260 may additionally include an inflow filter (not shown) to prevent entry of contaminants into the device 210, and thus to further protect the wound site. The pressure relief valve could operate in a variety of ways, including opening at a pre-set pressure point to allow ambient air to enter inside the housing 220 and closing after a pre-set pressure value is reached inside the housing 220, opening the device 210 and deactivating the vacuum source, or simply deactivating the vacuum source. It will be appreciated by those of skill in the art that the controlling the pressure within or without the device 10 includes turning on or off the vacuum source.

The wound healing device 210 may alternatively include a pressure controller for controlling the vacuum or pressure within the housing 220. The pressure controller may work in cooperation with a vacuum (pressure) sensor to detect the pressure within the wound cavity and/or over the wound within the liquid-retention chamber 240. The vacuum sensor is connected to the vacuum source 234 via a circuit board/relay combination and controls the vacuum source. The vacuum sensor may alternatively be coupled to the pressure relief (control) valve 260 to maintain therapeutic vacuum at the wound site. Vacuum (pressure) sensors or differential pressure sensors may provide a voltage output or a current output which signal can be used by a circuit board/relay combination to turn on or turn off the vacuum source. Examples of such electronic vacuum sensors are those commercially available from Honeywell under the trade name Sensotec sensors.

Alternatively, a vacuum switch or a differential pressure switch may be placed that shuts off the vacuum source 30 when the desired pressure is reached without any pressure relief valve. Such mechanical vacuum (pressure) switches are well known for practitioners of the art and can be purchased from MPL (Micro Pneumatic Logic), Air Troll, Air Logic among others.

In still other embodiments, the device 210 may include a fill indicator that indicates when the liquid-retention chamber 240 has a predetermined absorption level. The fill indicator 270 may operate in a variety of ways known to one of ordinary skill in the art. Such indicators include those that are visible (e.g., color change or LED) or audible. The fill indicator 270 may be advantageously placed on the external wall of the housing 220 or near the vacuum source 234. The fill indicator 270 may include a sensor component positioned inside the housing that communicates electronically or mechanically with the fill indicator. Such a sensor may be placed either between the liquid-retention chamber 240 and the liquid barrier 236 or on the wall of the liquid-retention chamber opposite to the wound interface 241. Some sensors operate by detecting presence of free moisture in the liquid-retention chamber 240, which denotes that the liquid-retention chamber has reached a predetermined absorption level. Alternatively, the fill indicator sensor may use electrical conductivity through a path in a portion of the liquid-retention chamber 240 to sense when moisture has reached the zone and provide a signal to shut off the vacuum source 230. Other sensors are known in the art and are suitable for use with the devices disclosed, including color-change technology based upon moisture content of the material or a change in a physical feature or characteristic, vacuum sensors based on detection of vacuum changes, galvanic, potentiometric, and capacitive types. The device 210 may additionally include an overflow valve such as a float valve for the vacuum connection to prevent transmission of liquid into the vacuum source.

The wound healing device 210 may also alternatively include a lack of vacuum or housing non-seal indicator or leak indicator (not shown). Such an indicator may be based on pump run-time, low vacuum signal from the vacuum sensor, visible indicators on the housing (e.g., a dimple on the housing that flattens or an embossed pattern on the housing that appears when the vacuum inside is at the appropriate level), low flow rate sensors, pressure sensitive color change, etc. The leak indicator may be in operable communication with the seal. The wound healing device 210 may also optionally include a sensor to detect oxygen levels or other gasses and a sensor to measure temperature at the wound site. The device 210 may also include a blood detector. In one embodiment, the blood detector may use optical technologies known in the art to detect the presence of blood within the housing 220.

In embodiments with sensors, other indicators, valves, switches, and the like, the adapter may be configured with channels, ports, inlets or outlets. For example, the adapter 232 may include communication leads from a vacuum sensor, fill indicator sensor, seal sensor or other sensors or indicators present in the interior of the housing 220. Further, any communications between a pressure relief valve or over-flow valve present on the housing 20 and the vacuum source can be channeled through such an adapter. In some embodiments, the adapter can also function as an on-off switch where the vacuum source as well as all the other components in the device will start functioning when the vacuum source is coupled to the housing 20 through the adapter.

Figure 7:
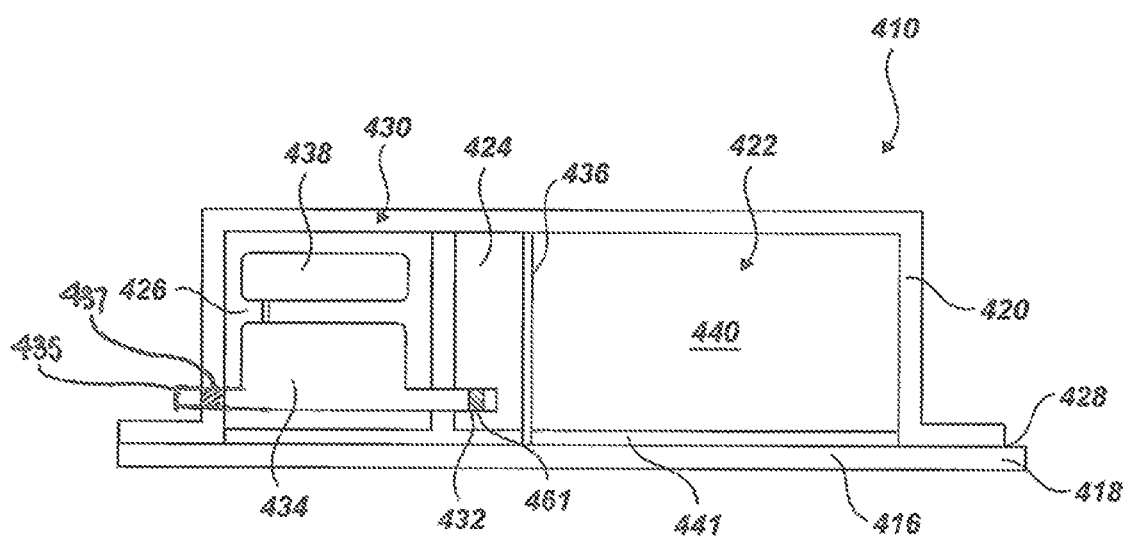
FIG. 7 is a side cross-sectional view of another alternative wound healing device including an internal vacuum pump as the vacuum source.

FIG. 7 illustrates yet another embodiment of a wound therapy device 410. Wound therapy device 410 offsets the vacuum source 434 and its associated power source 438 further from the wound site, which together may or may not be within the housing. In some situations, the offset may be beneficial for the wound. Similar to previous embodiments, the device 410 may include a housing 420 that encloses an internal space 422. This space 422 is subdivided into a vacuum chamber 424, a liquid-retention chamber 440, and an auxiliary chamber 426. As with previously-discussed embodiments, however, it is optional to include the auxiliary chamber 426, or to enclose the vacuum source 434 and power source 438 therein. When the vacuum source is an internally-placed vacuum pump 434, an outlet 435 is provided for the vacuum pump to vent. The outlet may include a filter 437 to prevent germs from outside from entering inside or vice-versa.

In this embodiment, the negative pressure source 430 extends through the housing 420 into the vacuum chamber 424 at an outlet 432. The outlet 432 may include a filter 461 (such as, in some embodiments, an antimicrobial filter) to prevent entry of wound exudate into the vacuum source 434. As with the other embodiments, this device 410 may include a liquid barrier 436, such as a hydrophobic membrane, that prevents flow of liquid into the vacuum chamber 424, but allows the negative pressure to extend into the liquid-retention chamber 440, causing liquid to be drawn into the liquid-retention chamber 440 from the wound. In some embodiments, the vacuum chamber 424 may include a porous hydrophobic foam. In other embodiments, the vacuum chamber 424 may be empty.

As described herein, the device 410 may be sealed to the body surface of a patient using either just the suction generated by the device 410 alone, or using a seal 428 chosen from those known to individuals skilled in the art. The seal 428 illustrated in FIG. 7 is an adhesive seal covered during storage by a cover 416, optionally including a pull tab 418. The device 410 may further include a wound interface 441 as similarly described herein.

Figure 8:
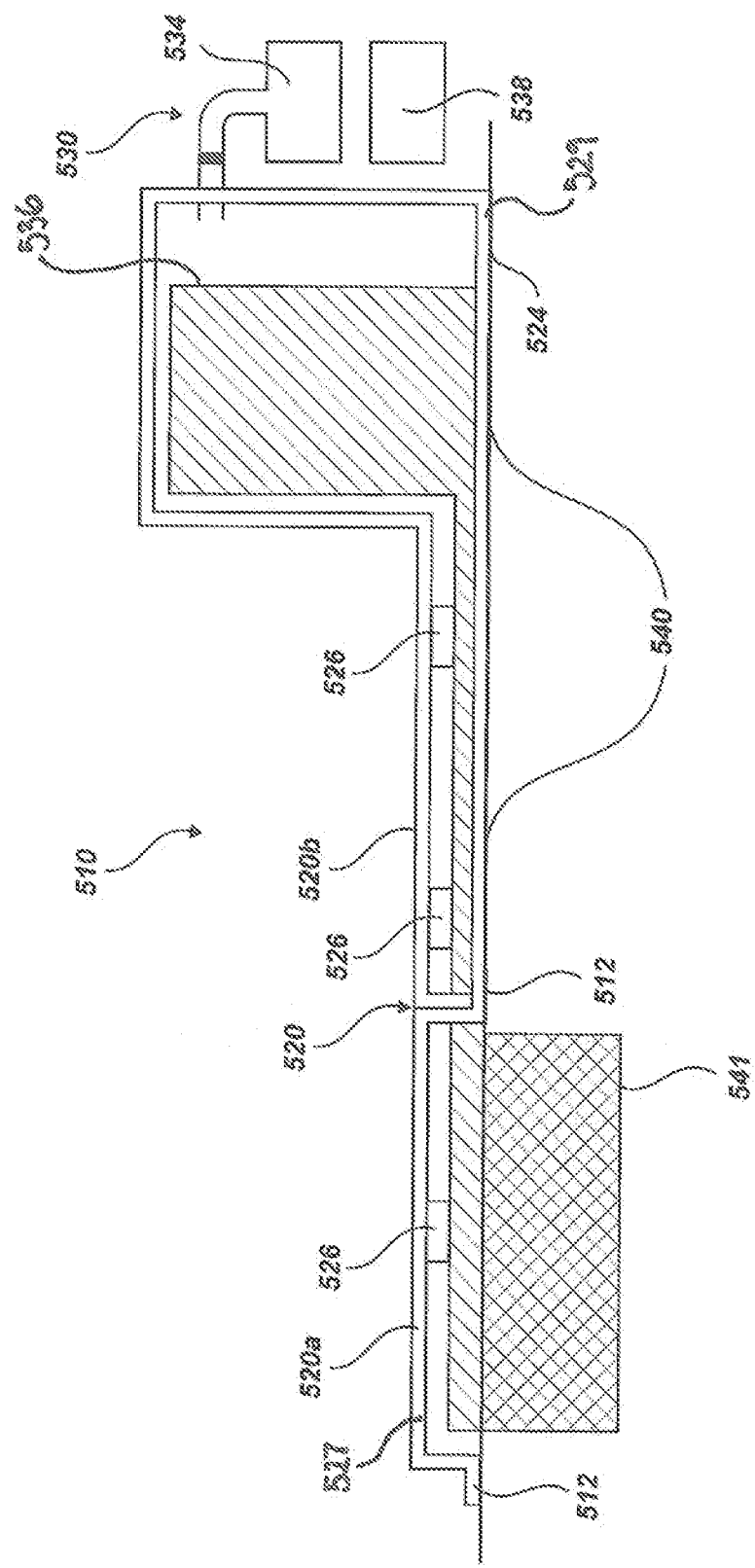
FIG. 8 is side cross-sectional view of another embodiment of a wound healing device with a housing of elongate shape.

FIG. 8 illustrates an alternative embodiment of a wound therapy device 510 that is applicable to assist in the healing of wounds located on parts of the body while standing, sitting, or laying, i.e., heel of the foot or buttock. In those instances it may be desirable that the wound site dressing and device components in the loaded areas substantially conform to the surrounding body so as to avoid pressure loading at the device site which may be detrimental to healing or could cause additional wounds. Furthermore, it may be desirable to collect wound liquid or exudate at a position remote from, but still adjacent the wound site.

To accomplish this, the device 510 shown in FIG. 8 has an elongated housing 520 structure with a proximal end 527 configured to cover at least a portion of the wound and a distal end 529 configured to be outside the wound perimeter. The wound interface 541 is located at the proximal end 527. In one embodiment, the vacuum source 530 is attached to the housing 520 adjacent the distal end 529. In another embodiment, the vacuum source 530 is attached to the housing 520 adjacent the proximal end 527. The liquid-retention chamber 540 extends from the wound interface 541 to the negative pressure source 530. In this embodiment a majority portion of the liquid-retention chamber 540 is at the end of the housing 520 adjacent the negative pressure source 530. The device 510 may also contain a liquid barrier 536 positioned between the liquid-retention chamber 540 and the vacuum or negative pressure source 530. In one embodiment, the liquid-retention chamber 540 extends from within a wound perimeter to a position outside the wound perimeter. In another embodiment, the housing 520 includes a proximal end 527 configured to cover at least a portion of the wound, and a distal end 529 configured to be outside a wound perimeter.

The wound interface 541 located at the wound site seals the wound and allows application of negative pressure to the wound site. The wound interface 541 may be in contact with the liquid-retention chamber 540 which extends to the location of the vacuum supply chamber 524. This extended liquid-retention chamber 540 allows the placement of the negative pressure source at a different location compared to a wound site.

Alternatively, the device 510 may have two separate housings: one housing 520a having a sealing surface 512 around the wound site and the other housing 520b being located at some distance away from the wound site. The latter housing 520b may or may not seal to the skin. Both housings 520a, 520b shown in FIG. 8 may be constructed of a liquid impermeable flexible barrier optionally supported by rigid or semi-rigid support structures 526. The housing 520b containing the vacuum chamber 524 may be located more conveniently where loading due to sitting, standing, or lying will not occur or can be substantially avoided. With a low aspect ratio, the device may be substantially planar over the wound site. In this configuration, pressure applied to the device will be distributed over a greater area and not be directed into the wound.

The negative pressure source 530 may include a micro-vacuum pump 534 operably coupled to a power source 538, such as a battery. The negative pressure source 530 may be external to the housing 520, as illustrated. However, it should be understood that alternative embodiments of the wound therapy device 510 may include the pump 534 which maybe a micro-vacuum pump and/or power source 538 internal to the housing 520. The negative pressure source 530 may be an osmotic or electroosmotic pump adjacent or internal to or adjacent the housing as discussed above.

Figure 9A:
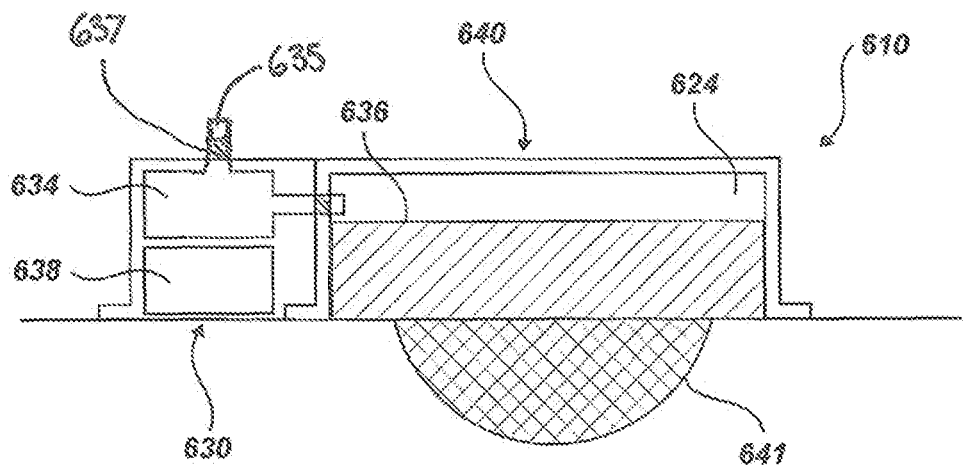
FIGS. 9A and 9B are schematic views of wound healing devices illustrating a modular approach to the device construction.
Figure 9B:
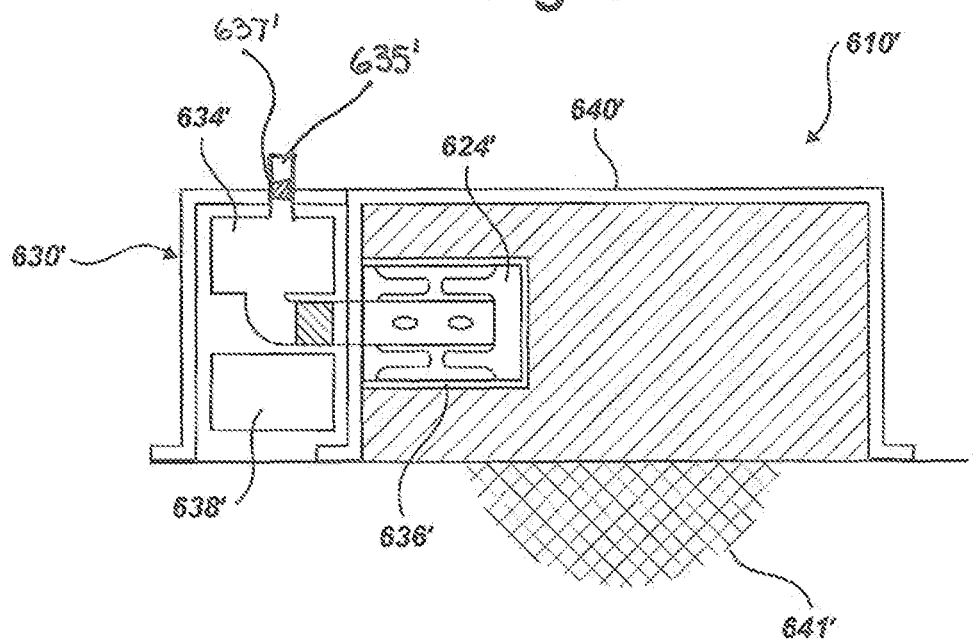

FIGS. 9A and 9B illustrate embodiments of a wound therapy device 610, 610' that are modular in nature. In this embodiment, the device 610, 610' may separate into three modules. However, greater or less than three modules may be used as would be apparent to one having skill in the art with the aid of the present disclosure. In the embodiments depicted, the device 610, 610' includes a wound interface module 641, 641', a liquid-retention module 640, 640', and a vacuum pump module 630, 630'. Due to its modular nature, any one of the modules or combination of modules of the device 610, 610' can be replaced as needed.

For example, if the liquid-retention module 640, 640' is filled to a predetermined level with exudate, it may be replaced with a new liquid-retention module 640, 640', while keeping the functional vacuum pump module 630, 630'. Alternatively, the liquid-retention module 640, 640' may be replaced at regular intervals to prevent overflow and assure appropriate capacity. Likewise, the wound interface module 641, 641' may be replaced independent of the other modules.

In the embodiment of FIG. 9A, the liquid-retention module 640 is similar in design to the embodiments depicted in FIGS. 2 and 6. The liquid-retention module 640' of FIG. 9B is similar in design to the embodiment depicted in FIGS. 3 and 4. Both embodiments of device 610, 610' include a liquid barrier 636, 636' to restrict exudate from entering into vacuum chamber 624, 624'. The vacuum pump module 630, 630' may include a vacuum source 634, 634', and optionally, a power source 638, 638'. When the vacuum source 634, 634' is internally placed, an outlet 635, 635' is provided for the vacuum source 634, 634' to vent. The outlet 635, 635' may include a filter 637, 637' to prevent germs from outside from entering inside or vice-versa.

The wound interface module 641, 641' of both embodiments may serve many functions as described above, such as being a layer or other structure that allows supply of vacuum to the wound while allowing easy and painless removal from the wound site during dressing changes. Alternatively, the wound interface may be a layer or other structure that provides beneficial bioagents in the form of specialized dressings such as dermal regeneration templates, bioabsorbable gels, foams and barriers that prevent tissue adhesion. The wound interface may also be a skin substitute, a layer for selectively maintaining moisture at the wound site, a layer that is angiogenic, and a layer that is antimicrobial. The wound interface may take a variety of forms, including, but not limited to a sheet, foam, gel, gauze or a porous matrix.

Figure 10:
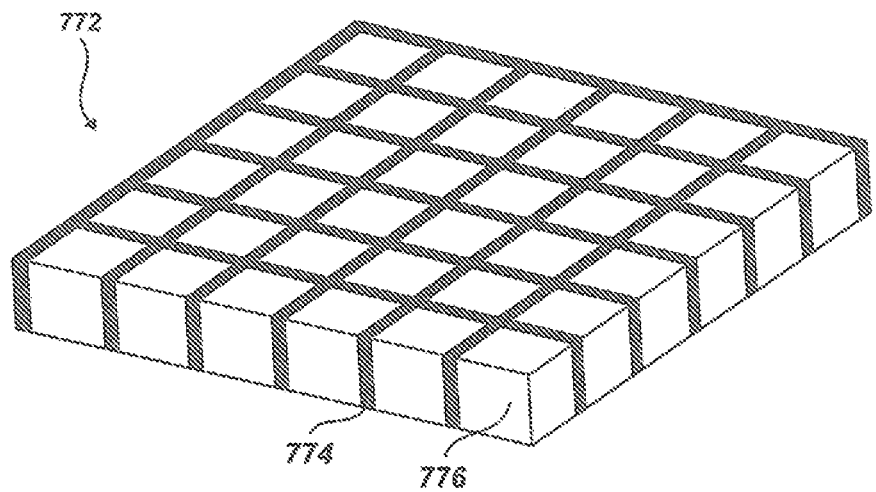
FIG. 10 is a perspective view of structural and absorbent material that may be disposed within a liquid-retention chamber of a wound healing device.

FIG. 10 illustrates a structural support 772 that may be disposed within the liquid-retention chamber of a wound therapy device. The structural support 772 may be shaped and/or customized to fit within the wound therapy device. The structural support 772 may include a structural support material 774 that is configured to provide support for the wound therapy device housing while under a negative pressure. The structural support material 772 may be constructed from rigid or semi-rigid plastics and the like. Disposed between the structural support material 774 is an absorbent material 776 for absorbing and retaining wound exudate within the liquid-retention chamber. As described above, the absorbent material 776 may include sponges; fibers, fabrics or gauzes; super-absorbent material including super-absorbent polymers; absorbent foams; gelling agents; packing and the like. In some embodiments, the absorbent material 776 may also serve as structural supports to the housing while the wound therapy device is under a negative pressure.

Figure 11:
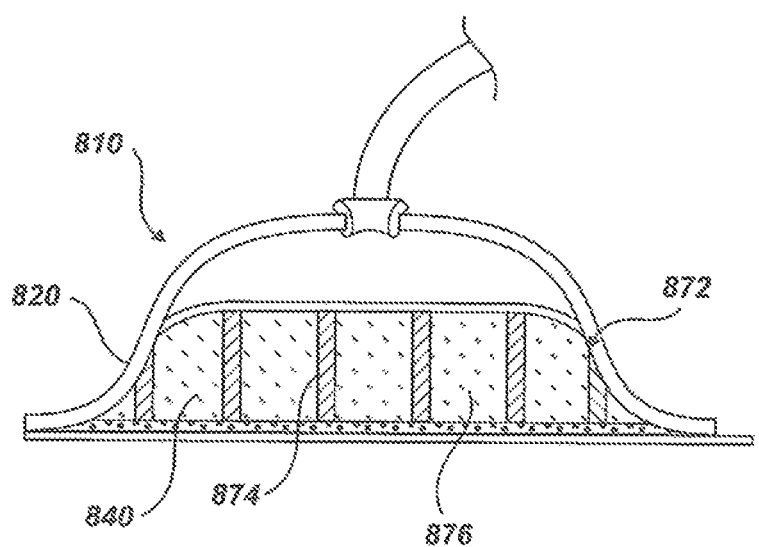
FIG. 11 is a side cross-sectional view of another embodiment of a wound healing device.

FIG. 11 represents another embodiment of a wound therapy device 810, similar to the embodiment depicted and described in conjunction with FIG. 2. The wound therapy device 810 may include a support structure 872 within the housing 820. As described in FIG. 10, the support structure 872 may include a structural support material 874 and an absorbent material 876 disposed within the liquid-retention chamber 840.

FIG. 12 shows a cross-sectional view of an alternate construction of the present wound therapy device. Device 910 includes a vacuum source module 911 and a dressing module 913, a coupling 948 maintains the vacuum source module 911 in communication with the dressing module 913. The coupling 948 is configured to transfer negative pressure generated by the vacuum source module 911 to the dressing module 913. The coupling 948 may be an adhesive pad. As discussed above, the coupling may be a feature of the dressing module 913 or the vacuum source module 911, or it may be a separate structure that allows the dressing module 913 to be connected to the housing module 911. This coupling may be accomplished by threaded engagement, snap fit, press fit, adhesion, welding, and the like. The dressing module 913 includes a housing 920 which for example may be a flexible barrier or surface wrap that defines an internal space 922. This internal space 922 may further include a vacuum chamber 924 and a liquid collector 940 separated by a liquid barrier 936. The vacuum chamber 924 in this case is a structural element such as a piece of plastic with void spaces or channels within for supplying vacuum to the liquid-retention chamber via the liquid barrier. It will be appreciated by those of skill in the art that the devices described in connection with FIGS. 1-11 may also be used in various configurations as the dressing modules 913, 1013, 1113, and 1213 of FIGS. 12-15.

The vacuum source module 911 includes a housing 933 containing a vacuum source 934, a vacuum switch 944 and a power supply 938. A vacuum source outlet 930 and a vacuum supply inlet 952 for the vacuum switch 944 are connected to the vacuum chamber 924 through the apertures 925 provided in the flexible barrier housing 920. The vacuum switch 944 can be replaced by a vacuum sensor/circuit board/relay combination. It is contemplated that the tubes can be releasably attached to the vacuum chamber to allow the modules 911 and 913 to be detached from one another.

FIG. 13 shows a cross-sectional view of a yet another construction of the present wound therapy device. Device 1010 includes a vacuum source module 1011, a dressing module 1013 and a coupling 1048 that maintains the vacuum source module 1011 in communication with the dressing module 1013. The dressing module 1013 includes a housing 1020 made of a flexible barrier/surface wrap which defines an internal space 1022. The internal space in this instance is occupied by the liquid-retention chamber 1040. Two apertures 1025 are provided on the housing 1020—one for connecting the vacuum supply and another for connecting a vacuum switch.

The coupling 1048 is configured to transfer negative pressure generated by the vacuum source module 1011 to the dressing module 1013. The coupling 1048 may include a lip or other structural element of either the vacuum source module 1011 or the dressing module 1013. The coupling 1048 may also be a separate member. The coupling allows the vacuum source module 1011 to be attached to and maintain communication with the dressing module 1013. In one embodiment, the vacuum source module 1011 is press fit into the dressing module 1013. In another embodiment, the dressing module 1013 is press fit into the vacuum source module 1011. The modules 1011 and 1013 may cooperate in threaded engagement with each other. The modules 1011 and 1013 may also be snap fit together or be bonded to one another in addition to other types of engagements. It will be appreciated by those of skill in the art that the modules 1011 and 1013 may be attached to each other in a variety of ways in order to practice the teachings of this invention.

The vacuum source module 1011 includes a housing 1033 containing a vacuum source 1034, a vacuum switch 1044 and a power supply 1038. The housing 1033 is provided with two apertures 1025—one for the vacuum outlet 1030 of the vacuum source 1034 and the other for the vacuum supply inlet 1052 for the vacuum switch 1044. Two liquid barrier films 1036 are positioned at apertures 1025. In one embodiment, the vacuum source module housing 1033 is attached to the dressing module housing 1020 using water-barrier adhesive 1048 such that the apertures in the first housing and the second housing lineup with the liquid barrier film in-between. This embodiment is different from earlier embodiments due to the absence of a vacuum chamber within the first housing, i.e. the vacuum connection 1030 is directly in communication with the liquid-retention chamber 1040 via the liquid barrier 1036. The vacuum switch can be replaced by a vacuum sensor/circuit board/relay combination. A fill indicator 1070 along with a sensor 1066 is also shown.

FIG. 14 shows a cross-sectional view of a yet another construction of the present wound therapy device. Device 1110 is thus shown to include a vacuum source module 1111 coupled to a dressing module 1113. The dressing module 1113 includes a housing 1120 made of a flexible barrier/surface wrap which defines an internal space 1122. The internal space in this instance is occupied by the liquid-retention chamber 1140. The vacuum source module 1111 is attached to the dressing module 1113 by a coupling 1132 or adapter 1132. The vacuum source module 1111 includes a vacuum source 1134, a vacuum sensor 1164 and a power supply 1138. The adapter 1132 contains a channel that connects a vacuum outlet 1130 from the vacuum source 1134 to a liquid barrier film 1136 present in the liquid-retention chamber 1140. The adapter 1132 also carries the communication channels between a vacuum sensor 1160 present in the liquid-retention chamber 1140 and a control module 1178 in the vacuum source module 1111. The control module 1178 may contain circuit boards and relays known in the art. Leads from a fill indicator sensor 1166, seal sensor (not shown) etc. present in the interior of the housing 1120 may also be part of the adapter 1132 or coupling 1032. Further, any communications between a pressure relief valve and an over-flow valve present on the housing 1120 and the vacuum source 1134 can be channeled through such an adapter 1132 or coupling 1132. In some embodiments, the adapter 1132 or coupling 1132 may also function as an on-off switch where the vacuum source 1134 as well as other components in the device will automatically start functioning when the module 1133 is coupled to the housing 1120 through the adapter 1132. The vacuum sensor/circuit board/relay can be replaced by a vacuum switch. A fill indicator 1170 along with a sensor 1166 is also shown.

FIG. 15 shows a cross-sectional view of yet another alternate construction of the present wound therapy device. Device 1210 is modular similar to the embodiments described in connection with FIG. 12-14 and includes a vacuum source module 1211 and a dressing module 1213. The dressing module 1213 includes an elongated housing 1220 made of a flexible barrier/surface wrap which defines an internal space 1222. The internal space in this instance is occupied by a liquid-retention chamber 1240 that may contain a liquid collector as discussed above. The dressing module 1213 includes a wound interface 1241 located at a proximal end of the housing 1220. A negative pressure source 1234 is located at the other or distal end outside the housing 1220. The liquid-retention chamber 1240 extends from the wound interface 1241 to the negative pressure source 1234. An adapter 1232 or coupling 1232 is provided between a housing 1233 of the vacuum source module 1213 and the housing 1220 of the dressing module 1213. The vacuum source module 1231 contains a vacuum source 1234, a pressure controller 1260 and a power supply 1238. The pressure controller may be in the form of a pressure relief valve and may be used to maintain negative pressure within the internal space 1222 of the housing 1220 (and thus within the retention chamber 1240 and at the wound surface 1241) at a therapeutic value. It will be appreciated by those of skill in the art that the pressure relief valve can be located anywhere on the device where the vacuum is established. The pressure relief valve may also be located on the vacuum source 1234 itself or on the vacuum connection 1230 (shown) or on the housing 1220.

The device 1210 may include a moisture disperser 1280 and a vacuum disperser 1282. The moisture disperser 1280 may facilitate even absorption of wound fluids by the liquid-retention chamber 1240 and/or liquid collector. The vacuum disperser 1282 may facilitate even distribution of vacuum within the liquid-retention chamber 1240 and/or liquid collector. Examples of such vacuum dispersion and moisture dispersers 1282, 1280 include the three-dimensional Knit Spacer Fabrics manufactured by Gehring Textiles. These spacer fabrics may include two separate face fibers that are combined, in a single knitting sequence, with an inner spacer yarn that has a relative perpendicular orientation to the face fibers. Face fibers can be made of, but are not limited to: cotton, nylon, polyester, neoprene, monofilament spandex, PBI, Nomex, Kevlar and fiberglass.

In one embodiment, the vacuum disperser is a surfactant applied to the liquid collector. The vacuum disperser may also be a hydrophobic structure positioned at the inlet of negative pressure into the housing 1220. It will be appreciated by those of skill in the art that the vacuum disperser may preclude the occlusion of the inlet by liquid collector material.

The retention chamber 1240 and/or the liquid collector 1242 may be single or multi layered. For example, it may be composed of the liquid collector 1242, the vacuum disperser 1282 and the moisture disperser 1280. These layers may be present between the liquid collector 1242 and the liquid barrier 1236 (or vacuum chamber 1224) or between the absorption layer 1242 and the wound bed.

Without limitation, it is believed that the disclosed devices and their methods of use may be useful for the therapy of surface wounds on a patient. These wounds may include, but are not limited to, infectious wounds, burn wounds, venous and arterial ulcers, diabetic ulcers and wounds, post-surgical wounds, bed sore wounds, and the like. Additionally, such devices are contemplated for use in a variety of fields, as would be contemplated by one of ordinary skill in the art.

According to one method of wound treatment or therapy utilizing the devices described herein, a device having a housing with a liquid-retention chamber is positioned above at least a portion of the wound. Negative pressure may be applied to the wound using the vacuum source. Wound liquids or exudate may be collected in the liquid-retention chamber. Additionally, the device may be replaced when it is filled with liquid. In modular embodiments, the liquid-retention chamber module, wound interface module, or the vacuum source may be replaced separately or in combination as needed.

A method of assembling a wound therapy device includes the steps of providing a vacuum source module comprising a vacuum source capable of generating negative pressure and a pressure controller for controlling the amount of negative pressure. The method also includes providing a dressing module having a housing to cover at least a portion of a wound site. The dressing module also includes a porous liquid collector positioned within the housing and in communication with the wound site. The liquid collector is configured to retain wound exudate while simultaneously communicating negative pressure generated by the vacuum source module to the wound site. The dressing module may also include a liquid barrier positioned between the liquid collector and the vacuum source module. The dressing module may further include a seal for sealing the dressing module to a surface around the wound site. The method includes securing the vacuum source module to the dressing module, such that the vacuum source module transfers negative pressure to the dressing module and attaching the device adjacent a wound site. It will be appreciated by those of skill in the art that the method steps may be practiced in a number of different orders to practice the teachings of the invention.

In some of the embodiments disclosed, the devices may be adapted to be inexpensive, light-weight, and either partially or entirely disposable. Further, the devices may be adapted to be simple to operate, such that in some instances, a patient could place the device with some reduced degree of medical supervision. In addition to the above, the devices may be constructed so as to be used without attention to their orientation.

It is contemplated that the devices may take a variety of forms, including those that are completely disposable when full, or partially disposable such as, for example, either the vacuum source or the liquid-retention chamber. In embodiments such as device 10 of FIGS. 1 and 2, it may be that the entire device may be discarded and replaced when filled. This may be convenient for smaller wounds, wounds that are already well along in the healing process, and wounds that are under home care. Such methods and apparatus prevent and/or reduce contact with potentially contagious or dangerous bodily liquids.

It should be noted that although the housings disclosed have been illustrated in particular shapes, such as being generally rounded, the housings are not necessarily limited to particular shape, and may be constructed in any advantageous shape. In some embodiments, the devices may be sized and shaped such that the vacuum chamber or liquid-retention chamber is capable of sealing over the patient's wound, at least in part. The housings and the seals disclosed may be configured to hold a vacuum when the device is placed and sealed over at least a portion of a wound on a patient's body surface. Such seals may be substantially air-tight to prevent the entry of microbes but do not need to be absolutely impermeable. It is contemplated that vacuum pressure will either be continuously or periodically applied to maintain a therapeutic negative pressure therapy range.

When the vacuum is switched on after placing the device on a patient's wound, air is removed around the wound, generating a vacuum within the housing cavity. At the same time, wound-liquid absorbing material may begin absorbing the exudate/liquids in the wound. Sustained negative pressure over a wound region may promote tissue migration and wound closure. In some embodiments, the devices may be shaped like a patch or bandage that may be changed more than once a day. It will be appreciated by those of skill in the art that the device may continue to absorb and trap fluid when the device or vacuum is switched off.

Additionally, the device may contain a fill indicator that senses the presence of free moisture in the liquid-retention chamber that signals that the optional porous pad has reached a predetermined absorptive level. The fill indicator may in turn be coupled to an over-flow valve to prevent wound liquids from reaching the vacuum pump or it may provide a signal used to prompt disabling the pump.

In all of the above embodiments, when the devices are adapted to be disposable, they may be discarded after use in part or in whole. Indeed multiple disposable devices can be provided to a patient for a treatment plan, which may consist of a plurality of individual treatments with disposable devices over a predetermined period.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. Note that elements recited in means-plus-function format are intended to be construed in accordance with 35 U.S.C. §112 ¶6. The scope of the invention is therefore defined by the following claims.

The invention claimed is:

1. A wound therapy device, comprising:
   a liquid-retaining structure adapted to be positioned at a tissue site and configured to absorb liquid from the tissue site;
   a source of negative pressure configured to be in fluid communication with the liquid-retaining structure and configured to deliver a reduced pressure to the tissue site;
   a vacuum disperser layer configured to be positioned between the liquid-retaining structure and the source of negative pressure, wherein the vacuum disperser layer is configured to distribute vacuum within the liquid-retaining structure; and
   a liquid barrier configured to be positioned between the liquid-retaining structure and the source of negative pressure.

2. The wound therapy device of claim 1, further comprising an interface layer adapted to be positioned at the tissue site.

3. The wound therapy device of claim 2, wherein the interface layer further comprises a pouch comprising porous beads.

4. The wound therapy device of claim 1, wherein the liquid-retaining structure comprises a superabsorber.

5. The wound therapy device of claim 1, further comprising a wound cover configured to cover the liquid retaining structure.

6. The wound therapy device of claim 5, wherein the wound cover is positioned over the source of negative pressure and the liquid-retaining structure.

7. A wound therapy device, comprising:
a flexible wound cover configured to cover at least a portion of a tissue site;
a liquid-retaining structure configured to absorb wound exudate positioned under the wound cover;
a disperser layer configured to be positioned over the tissue site;
a liquid barrier configured to retain liquid within the wound cover; and,
a wound interface positioned beneath the liquid retaining structure and the disperser layer.

8. The wound therapy device of claim 7, further comprising a source of negative pressure.

9. The wound therapy device of claim 8, wherein the source of negative pressure is mounted to the flexible wound cover.

10. The wound therapy device of claim 8, wherein the flexible wound cover further comprises a fluidic connector configured to transmit negative pressure from the source of negative pressure to the tissue site.

11. The wound therapy device of claim 7, wherein the liquid-retaining structure further comprises a cellulose material.

12. The wound therapy device of claim 7, further comprising a seal configured to seal the wound therapy device to the body.

13. The wound therapy device of claim 7, further comprising a saturation indicator for indicating absorption of liquid within the liquid-retaining structure.

14. The wound therapy device of claim 7, wherein the disperser layer comprises a moisture disperser layer positioned below the liquid-retaining structure, the moisture disperser layer configured to distribute liquid within the liquid-retaining structure.

15. A method of treating a wound, comprising:
positioning a wound dressing over at least a portion of a wound, the wound dressing comprising a liquid-retaining structure and a disperser layer; and
applying negative pressure to the wound through the wound dressing, wherein negative pressure is applied to the wound dressing using a negative pressure source;
wherein when negative pressure is applied the liquid-retaining structure absorbs wound exudate and the disperser layer distributes fluid within the liquid-retaining structure, and the wound dressing comprises a liquid barrier positioned between the liquid-retaining structure and the negative pressure source that prevents liquid from traveling from the liquid-retaining structure to the negative pressure source, while the liquid-retaining structure simultaneously communicates negative pressure generated by the negative pressure source to the wound.

16. The method of treating a wound of claim 15, wherein the wound dressing further comprises a flexible wound cover.

17. The method of treating a wound of claim 15, wherein the disperser layer is located beneath the liquid-retaining structure.

18. The method of treating a wound of claim 15, wherein the wound dressing further comprises a flexible wound cover and a wound contact layer, wherein the flexible wound cover and the wound contact layer are configured to enclose the liquid retaining structure and the disperser layer, such that the wound dressing is applied to the wound as a single unit.

19. The method of claim 15, further comprising detecting a change in negative pressure at the wound using an indicator.

20. The method of claim 19, wherein the indicator is configured to change color.

21. The method of claim 17, wherein the wound dressing further comprises a vacuum disperser layer positioned above the liquid-retaining structure, wherein the vacuum disperser layer distributes vacuum within the liquid-retaining structure when negative pressure is applied.

22. The wound therapy device of claim 5, wherein the liquid barrier is underneath the wound cover.

23. The wound therapy device of claim 1, further comprising a moisture disperser layer positioned below the liquid-retaining structure, the moisture disperser layer configured to distribute liquid within the liquid-retaining structure.

24. The wound therapy device of claim 1, further comprising an indicator configured to detect a change in negative pressure at the tissue site.

25. The wound therapy device of claim 24, wherein the indicator is configured to change color.

26. The wound therapy device of claim 7, wherein the disperser layer comprises a three dimensional knit.

27. The wound therapy device of claim 7, wherein the disperser layer comprises a vacuum disperser layer positioned above the liquid-retaining structure, the vacuum disperser layer configured to distribute vacuum within the liquid-retaining structure.

28. The wound therapy device of claim 27, further comprising a moisture disperser layer positioned below the liquid-retaining structure, the moisture disperser layer configured to distribute liquid within the liquid-retaining structure.

29. The wound therapy device of claim 7, wherein the liquid-retaining structure comprises a super-absorbent polymer.

30. The wound therapy device of claim 7, wherein the liquid barrier is located beneath the wound cover.

31. The wound therapy device of claim 7, further comprising an indicator configured to detect a change in negative pressure at the tissue site.

32. The wound therapy device of claim 31, wherein the indicator is configured to change color.

* * * * *